United States Patent
Bustamante

(10) Patent No.: US 9,835,607 B2
(45) Date of Patent: Dec. 5, 2017

(54) SYSTEM AND METHOD FOR TESTING TRANSFORMER OIL

(71) Applicant: DGA Plus, Inc., Whittier, CA (US)

(72) Inventor: Jorge Antonio Bustamante, Whittier, CA (US)

(*) Notice: Subject to any disclaimer, the term of this patent is extended or adjusted under 35 U.S.C. 154(b) by 108 days.

(21) Appl. No.: 14/921,695

(22) Filed: Oct. 23, 2015

(65) Prior Publication Data

US 2016/0146711 A1 May 26, 2016

Related U.S. Application Data

(60) Provisional application No. 62/067,853, filed on Oct. 23, 2014.

(51) Int. Cl.
*G01N 33/28* (2006.01)
*G01N 1/10* (2006.01)
*G01N 1/20* (2006.01)

(52) U.S. Cl.
CPC .......... *G01N 33/28* (2013.01); *G01N 1/2035* (2013.01); *G01N 2001/1037* (2013.01)

(58) Field of Classification Search
CPC ... G01N 33/28; G01N 1/10; G01N 2001/1031
USPC .............. 73/863.71, 863.85, 863.8
See application file for complete search history.

(56) References Cited

U.S. PATENT DOCUMENTS

| | | | | |
|---|---|---|---|---|
| 1,838,729 A * | 12/1931 | Andrews | ............ | G01N 1/12 137/327 |
| 3,017,772 A * | 1/1962 | Rondle | ............ | G01N 30/20 73/23.42 |
| 4,056,981 A * | 11/1977 | Kalka | ............ | B01J 3/02 73/863.85 |
| 4,350,052 A * | 9/1982 | Kendall | ............ | G01N 1/10 137/318 |
| 4,598,731 A * | 7/1986 | Colson | ............ | F16K 13/04 137/318 |
| 4,712,434 A * | 12/1987 | Herwig | ............ | G01N 1/2035 73/863.71 |
| 4,715,236 A * | 12/1987 | Willert | ............ | G01N 1/2035 73/863.86 |
| 5,116,330 A * | 5/1992 | Spencer | ............ | G01N 1/2035 73/863.71 |
| 5,131,282 A * | 7/1992 | Kuhner | ............ | G01N 1/2035 73/863.71 |
| 5,131,283 A * | 7/1992 | Canfield | ............ | G01N 1/2035 137/318 |
| 5,251,495 A * | 10/1993 | Kuhner | ............ | G01N 1/2035 73/863.71 |
| 5,351,563 A * | 10/1994 | Karpf | ............ | G01N 21/05 204/409 |

(Continued)

*Primary Examiner* — Peter Macchiarolo
*Assistant Examiner* — Alexander Mercado
(74) *Attorney, Agent, or Firm* — Larisa Migachyov

(57) ABSTRACT

A system and method for testing the oil in a transformer, comprising attaching a threaded shaft to the wall of the oil tank at a height sufficient to avoid the sediments that accumulate on the bottom of the oil tank, drilling a small hole through the stud into the tank, attaching a ball valve to the stud, and filling a double-ended glass vial through the hole. The double-ended glass vial preferably comprises a cap with a tapered barbed stem incorporating a shut off valve that can be connected to the ball valve port by means of simply processing the tapered barb stem into the ball valve port.

9 Claims, 4 Drawing Sheets

(56) References Cited

U.S. PATENT DOCUMENTS

| | | | | |
|---|---|---|---|---|
| 5,361,643 | A * | 11/1994 | Boyd | G01N 1/2035 73/863.71 |
| 5,370,005 | A * | 12/1994 | Fjerdingstad | G01N 1/2035 73/863.71 |
| 5,408,889 | A * | 4/1995 | Parault | G01N 1/12 73/863.71 |
| 5,594,182 | A * | 1/1997 | Jansen | G01N 1/10 73/863.71 |
| 5,600,075 | A * | 2/1997 | Peterson | G01N 1/22 73/863.71 |
| 5,945,611 | A * | 8/1999 | Welker | G01N 1/2035 73/863.71 |
| 6,199,436 | B1 * | 3/2001 | Morel | G01N 1/10 73/864.52 |
| 8,776,622 | B2 * | 7/2014 | Briscoe | G01N 1/2273 73/31.02 |
| 2004/0099068 | A1 * | 5/2004 | Welker | G01N 1/2226 73/863.71 |

* cited by examiner

SYSTEM AND METHOD FOR TESTING TRANSFORMER OIL

CROSS-REFERENCE TO RELATED APPLICATIONS

The present application takes priority from Provisional App. No. 62/067,853, filed Oct. 23, 2014, which is herein incorporated by reference.

BACKGROUND

Electrical transformers are large devices that are typically cooled and insulated by mineral oil. Many such transformers, large power, pad-mounted and pole-mounted, are used in the electric power industry. The mineral oil serves as a coolant and also suppresses corona and arcing and insulates various internal electrically energized parts. Since transformer oils are subject to electrical, thermal and mechanical stresses while a transformer is in operation, as well as being contaminated by chemical interactions with copper or aluminum windings and other solid insulation, it is important to test the oil regularly to ensure the continued operability of the transformer and the effectiveness of the oil. Such testing can measure the amount of dissolved gas in the oil that has emulsified during adverse operating conditions, various contaminants present in the oil, or any other indications of sparking, wear, high temperatures, or other transformer damage caused by environmental conditions.

Typically, the oil tank on a transformer has a large valve close to the bottom of the tank. To test the oil, a worker has to open the valve and fill a sample container with oil; the sample container is then taken to a laboratory to be tested. The sample containers comprise of a metal or plastic valve that allows the oil to flow in but prevents it from flowing out. These containers are common syringe design, constructed of glass.

This method has several problems. The oil in a transformer tends to contain sediment that settles close to the bottom of the tank. To draw out a usable sample, a worker has to flush the system sufficiently that the sample is free of sediment and contaminants. This results in a lot of oil being simply wasted, and a much lengthier, more expensive, and more complicated process for taking the sample. The fact that each container, glass or metal has to incorporate a valve in the cap and makes the containers more expensive as well. Due to the expense and complexity of the process, many transformers are simply not tested at all, which has negative impact to the equipment's reliability and is dangerous.

A need therefore exists for a simpler, quicker, and less expensive system and method for taking oil samples from a transformer.

LIST OF FIGURES

SUMMARY OF THE INVENTION

An object of the present invention is to provide a method and system for taking oil samples from a transformer without wasting excess oil.

Another object of the present invention is to provide a method and system for taking oil samples from a transformer in a quick and easy way.

In the preferred embodiment of the method of the present invention, a threaded shaft is attached to the wall of the oil tank of a transformer. The threaded shaft may comprise a hole through its central axis in an embodiment. Tooling is then attached to the threaded shaft, and a hole is drilled through the central axis of the threaded shaft and the wall of the oil tank. A valve is then attached to the threaded shaft, and left closed until testing is needed. The valve is preferably a ball valve. When the testing process begins, a glass sample vial is attached to the valve, where the glass sample vial is open on both ends. Oil is allowed to flow through the glass sample vial until all the excess contaminants and sediments are flushed out. When that is true, the glass sample vial is sealed on the free end, filled with oil, and detached from the valve and sealed on the other end.

Since sediments tend to collect at the bottom of the tank, the threaded shaft is preferably attached at a height between 24" and 48" from the bottom of the tank. However, any other height is also acceptable for practicing the method of the present invention.

The threaded shaft is preferably attached to the wall of the oil tank by a capacitance discharge weld. Any other method of attachment may also be used as long as it is secure and leakproof. In an embodiment, the threaded shaft comprises a base that is wider than the diameter of the threaded shaft, which is attached to the wall of the oil tank.

In an embodiment, the first opening of the glass sample vial comprises a cap with a barb tip that comprises a shut-off valve.

The step of sealing the glass sample vial at the second end comprises attaching a cap to the second end of the glass sample vial; the cap can be any cap that can securely seal the glass sample vial.

DETAILED DESCRIPTION OF THE PREFERRED EMBODIMENT

Figure 1:
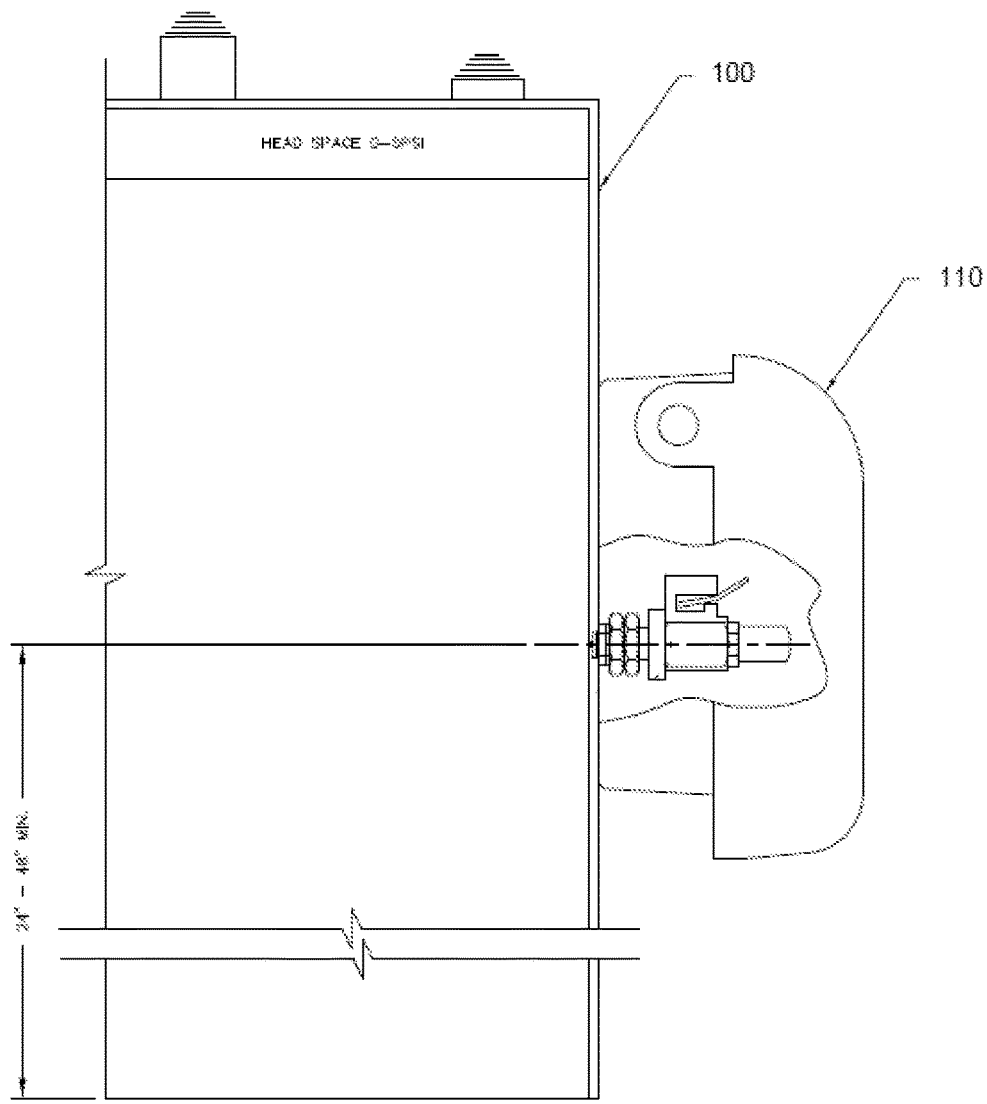
FIG. 1 shows a cross sectional view of the shaft and valve of the present invention, installed on the wall of an oil tank.

FIG. 1 shows a diagram of the testing port installed by the method of installation of the preferred embodiment of the present invention. The method of the present invention preferably comprises the following steps, though it will be understood by a person of reasonable skill in the art that all the steps described below it could be replaced by reasonable equivalents thereof, and that not all the steps need to be performed for each individual embodiment of the present invention.

As shown in FIG. 1, the assembly of the present invention is preferably installed at a height of 24-48" above the bottom of the oil tank 100 of a transformer. Installing this assembly at this height range prevents sediments that settle near the bottom from getting into the oil sample. While this height range is preferable, the invention is not limited to this particular height range. A weather cover 110 is preferably used to cover the assembly when not in use.

Figure 2:
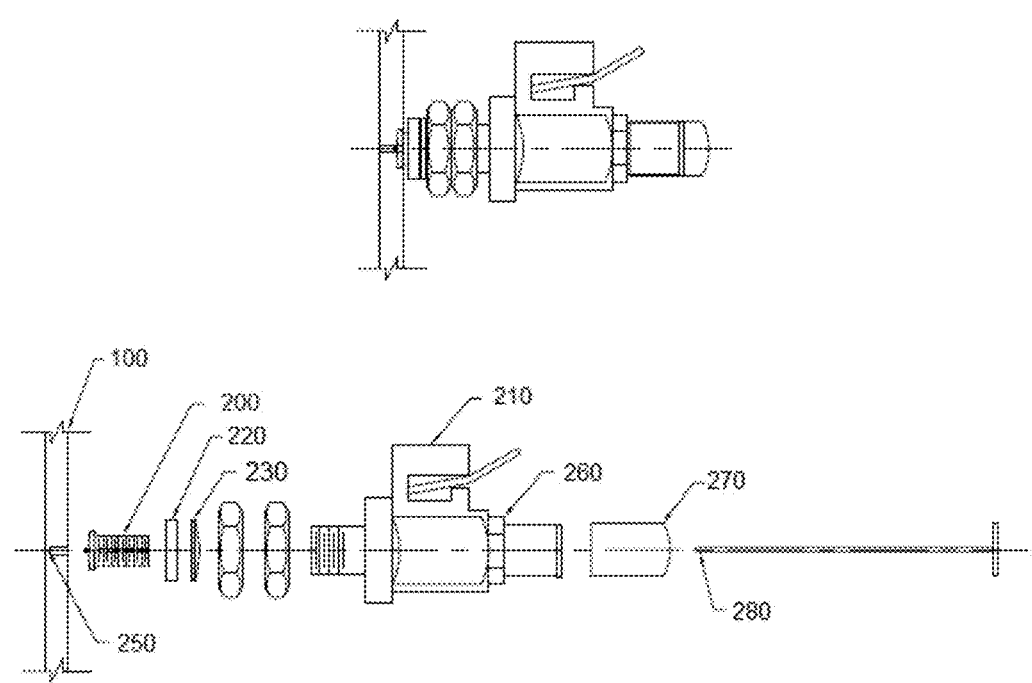
FIG. 2 shows an exploded view of the shaft and valve of the present invention.

FIG. 2 shows a close-up view of the assembly installed by the method of the present invention. The first step of the method is attaching a threaded shaft 200 to the wall of the transformer tank 100. The threaded shaft 200 is preferably attached by a capacitance discharge weld in order to be leakproof and secure without burning the oil; it is preferably ¼" in diameter, but can be any other size.

In an embodiment, the threaded shaft is pre-drilled with a hole. This simplifies the drilling task and eliminates metal shavings in the oil tank. The oil tank may also be pre-drilled part of the way (see ref no. 250) through the thickness of the tank wall to reduce the amount of metal shavings. The pre-drilling is preferably to within $\frac{1}{32}$" prior to entering the tank oil system.

Next, a ball valve 210 is attached to the threaded shaft, as shown in FIG. 2. The ball valve is screwed onto the threaded shaft as shown. In the preferred embodiment, rubber sealing washers 220 and 230 are used between the ball valve 210 and the wall of the tank 100, as shown in the unexploded view of FIG. 2. This prevents any leaking and makes for a more secure attachment.

Figure 4:
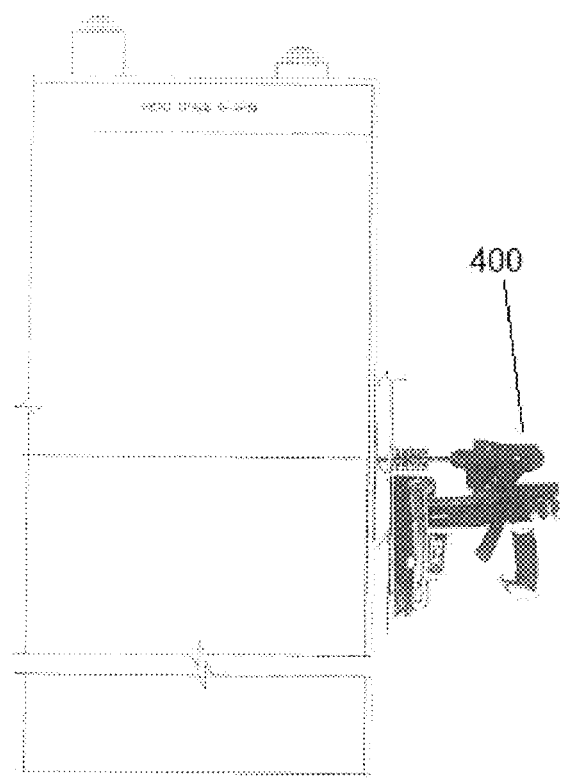
FIG. 4 shows a view of the tooling used to drill a hole through the central axis of the threaded shaft of the present invention.

A piercing tool gland nut 260 and piercing tip gland seal 270 is then attached to the end of the ball valve 210. After that is done, a piercing tip 280 is passed through the valve and used to pierce through the tank wall, using the hole in the threaded shaft as a guide. The piercing tip is preferably a $\frac{1}{16}$" chrome vanadium steel drilling tip with a 120° angle, but any other drilling/piercing implement may be used. FIG. 4 shows the tooling 400 used to pierce through the tank wall.

In the preferred embodiment, as shown in FIG. 2, the threaded shaft comprises a base that is wider than the rest of the shaft. This makes for a more secure attachment between the threaded shaft and the wall of the oil tank.

The ball valve and shaft assembly are left on the wall of the oil tank permanently. The valve is closed to prevent any leakage from the oil tank.

When a sample needs to be taken, a glass vial is connected to the valve to take the sample. The glass vial is preferably a sufficient size to contain the volume of oil needed for lab analysis. While it is not required to practice the method of the present invention, in the preferred embodiment, the glass vial is a two-ended vial with openings on both ends. Each end enables the operator to flow some fluid out before taking the sample, to get rid of stray contaminants and make sure there are no foreign substances or air bubbles in the sample. The fact that the vial is made of glass means that an operator can see through it and verify that there is no air in the sample and that the sample is relatively free of foreign substances. However, other materials are also acceptable, as long as they are non-reactive with transformer oil, stable, and transparent or translucent.

Figure 3:
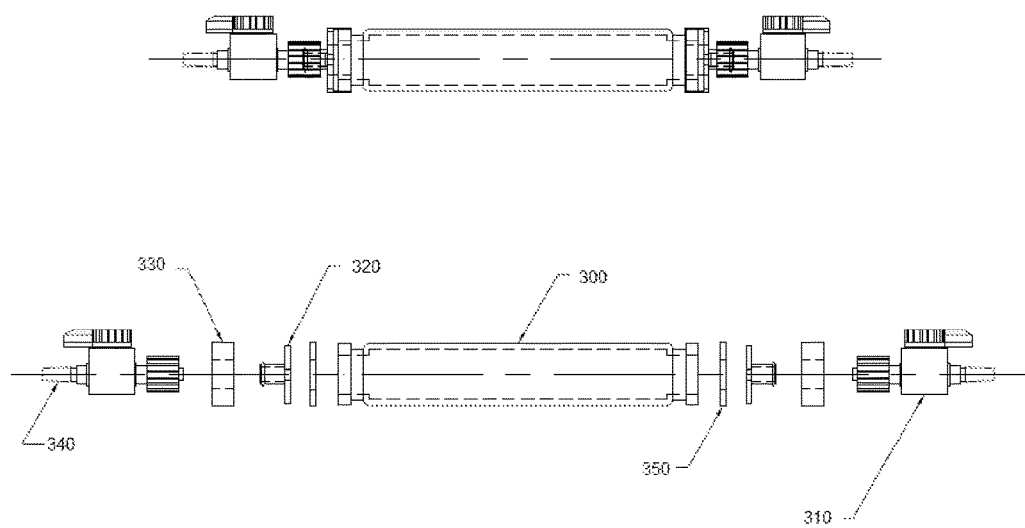
FIG. 3 shows a view of the glass vial of the present invention.

FIG. 3 shows a sample two-ended glass vial 300 of the type used in the preferred embodiment of the present invention. The glass vial 300 comprises two cap assemblies, one on each end. In the preferred embodiment, each cap assembly comprises a luer stopcock 310 with a barb tip 340. As shown in the Figure, each opening of the glass vial comprises a lip around the edge. A luer heel tip 320 is placed on the opening, and a serum cap 330 is crimped around the luer heel tip 320 and the lip to hold it in place. A washer 350 is preferably placed between the luer heel tip 320 and the opening of the glass vial to prevent leaking. The luer stopcock 310 is then connected to the luer heel tip 320.

In order to collect a sample, the barb tip 340 on one end of the glass vial is connected to the ball valve installed on the tank via a piercing tip gland seal or any other connector that allows oil to flow through. The opposite end of the glass vial may be fitted with plastic tubing for draining and flushing. The ball valve is then opened and oil is allowed to flow through the glass vial and out the other end of the glass vial. The operator preferably observes the oil as it flows through the glass vial to determine whether it contains foreign particles or air bubbles.

Once the oil flowing through the glass vial is free of foreign particles or air bubbles, the operator seals the free end of the glass vial by closing off the stopcock tip on that end. Oil is then allowed to fill the glass vial.

Once the glass vial has been filled, the welded tank ball valve and the valve in the other stopcock tip are closed to seal the off the sample flow and contain the sample in the glass vial. In the preferred embodiment, a label is printed out by the operator and adhered to the vial to identify it and track it onto the laboratory for analysis.

While the luer connectors shown in the Figure are the preferred embodiment of the present invention, other connectors and valves may also be used. In an embodiment, rather than using a stopcock tip, the operator simply crimps a serum cap on the free end of the glass vial, fills it, and then closes off the welded tank ball valve, removes the glass vial, and seals the other end by a similar serum cap. In an embodiment, the glass vial comprises screw threads on each opening so that a screw-on cap may be used.

A sample embodiment is described above. It will be understood that the invention comprises other embodiments that are equivalent to the embodiment described.

The invention claimed is:

1. A method of testing the oil in an oil tank of a transformer, comprising:
   permanently attaching a threaded shaft to the wall of the oil tank, the threaded shaft comprising a central axis;
   fastening a valve to the threaded shaft;
   attaching tooling to the threaded shaft for drilling a hole through the central axis of the threaded shaft;
   drilling a hole through the central axis of the threaded shaft and the wall of the oil tank;
   attaching a glass sample vial to the valve, said glass sample vial comprising a first end and a second end, wherein the first end is attached to the valve, wherein the glass sample vial comprises an opening on the first end and an opening on the second end;
   letting oil flow through the glass sample vial, flowing into the opening on the first end and out of the opening on the second end;
   sealing the glass sample vial at the second end;
   removing the glass sample vial from the valve;
   sealing the glass sample vial at the first end,
   wherein the valve is a ball valve comprising a piercing tip gland seal, wherein the glass sample vial comprises a first stopcock valve and a first stopcock barb tip on the first end and a second stopcock valve and a second stopcock barb tip on the second end, wherein the step of attaching a glass sample vial to the valve comprises:
   poking a small hole in the piercing tip gland seal;
   inserting the first stopcock barb tip into the small hole;
   opening the ball valve;
   opening the first stopcock valve.

2. The method of claim 1, wherein the step of sealing the glass vial on the second end comprises closing the second end stopcock valve, the step of sealing the glass vial on the first end comprises closing the first end stopcock valve and closing the ball valve, and the step of removing the glass vial from the valve comprises removing the stopcock barb tip from the gland seal and replacing the gland seal with a new one.

3. The method of claim 1, wherein the threaded shaft is attached to the oil tank at a height between 24" and 48" from the base of the oil tank.

4. The method of claim 1, wherein the threaded shaft is attached to the wall of an oil tank by a capacitance discharge weld.

5. The method of claim 1, wherein the threaded shaft comprises a base that is wider than the diameter of the threaded shaft, wherein the base is attached to the wall of the oil tank.

6. The method of claim 1, wherein the glass sample vial is shaped like a tube.

7. The method of claim 1, wherein at least one of the openings of the glass sample vial comprises a flange for attaching a serum cap to the opening.

8. The method of claim 1, wherein at least one opening of the glass sample vial comprises:
   a cap assembly comprising a barb tip, wherein the barb tip comprises a shut-off valve.

9. The method of claim 1, wherein the step of sealing the glass sample vial at the second end comprises:
   attaching a cap assembly to the second end of the glass sample vial.

\* \* \* \* \*